April 16, 1940. L. PAHISSA Plant Pat. 379
ROSE PLANT
Filed Aug. 22, 1939
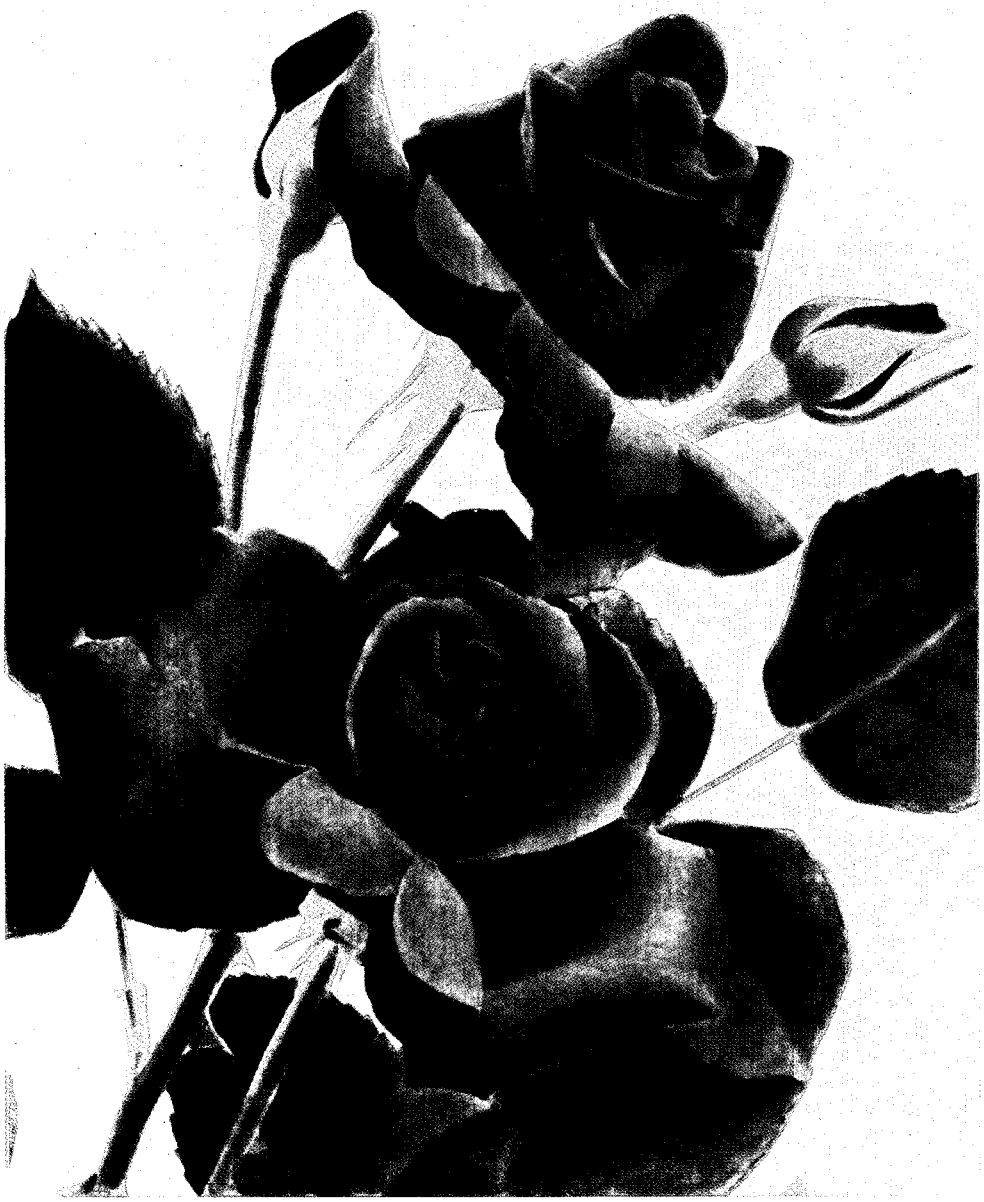
Inventor
L. Pahissa
By Robb & Robb
attorneys Patented Apr. 16, 1940

Plant Pat. 379

UNITED STATES PATENT OFFICE

379

ROSE PLANT

Lorenzo Pahissa, San Feliu de Llobregat, Spain, assignor to Jackson & Perkins Company, Newark, N. Y.

Application August 22, 1939, Serial No. 291,448

1 Claim. (Cl. 47—61)

This invention relates to a new and distinct variety of Hybrid Tea Rose plant.

The new rose depends primarily for distinctiveness upon the deep rich Ox Blood Red color of its flower changing to deep Carmine at the end of three days and the symmetrical form of bud and half open flower in that color. The deeply notched petals and the medium height semi-compact growth of the bush, together with the color of the wood, foliage and thorns are also notable features of distinction.

Other important features of novelty are noted in the following detailed description, in which the color terminology employed is in accordance with Ridgway's Standard Chart.

Parentage:

*Seed parent.*—Unnamed seedling (Mme. Edouard Herriott × Angele Pernet).

*Pollen parent.*—Mari Dot.

Classification:

*Botanic and commercial.*—Hybrid Tea.

*Flower*

Observations made in the morning of June 30, 1939, at Newark, New York.

Blooming habit:

*Recurrent.*—Continuous.

Bud:

*Size.*—Medium.

*Form.*—Pointed. Is not affected by hot or wet weather.

*Color.*—When sepals first divide—Ox Blood Red, Plate 1. When petals begin to unfurl—Ox Blood Red, Plate 1. When half blown: inside of petals—Ox Blood Red to Carmine, Plate 1; reverse of petals—Carmine, Plate 1.

*Sepals.*—Serrated, branched. Curl back when half open.

*Calyx.*—Shape—funnel. Size—broad. Aspect—smooth.

*Peduncle.*—Length — medium. Aspect — smooth. Color—Light Cress Green, Plate 31, overcast with Vandyke Red, Plate 13. Strength—erect, heavy.

*Opening.*—Bud opens well. Is not affected by adverse conditions.

Bloom:

*Size.*—Medium. Average size when fully expanded—4½".

*Borne.*—Several together.

*Stems.*—Medium length, strong.

*Form.*—When first open—globular. Permanence—flattens.

*Petalage.*—Double (full but open center). Number of petals under normal conditions—25.

*Color.*—Center of flower—Ox Blood Red, Plate 1. Outer petals—Ox Blood Red to Carmine, Plate 1. Base of petals (aiglet)—Pinard Yellow, Plate 4. Inside of petals—Ox Blood Red, Plate 1. Reverse of petals—Carmine. General tonality from a distance—Dark Red.

*Discoloration.*—General tonality at end of first day—Ox Blood Red, Plate 1. Second day—Ox Blood Red to Carmine, Plate 1. Third day—Carmine, Plate 1.

Petals:

*Texture.*—Thick. Is not affected by wet or hot weather.

*Appearance.*—Inside—velvety. Outside—satiny.

*Form.*—Scalloped.

*Arrangement.*—Informal (with "rags" in center). Petaloids in center—few, small.

*Persistence.*—Drop off cleanly.

*Fragrance.*—Strong. Nature—"Old Rose perfume" (Centifolia).

*Lasting Quality.*—On the plant and as cut flower—fair.

Genital organs:

*Stamens, anthers.*—Size—medium, many. Color—White, Antimony Yellow, Plate 15. Arrangement—regular around styles.

*Stamens, filaments (threads).*—Size—medium length. Color—Light Jasper Red, Plate 13.

*Pollen.*—Warm Buff, Plate 15.

*Styles.*—Bunched, medium length.

*Stigmas.*—Pinard Yellow, Plate 4.

*Ovaries.*—All enclosed in calyx.

Fruit: Variety is fertile with its own pollen.

*Form.*—Ovoid, flat headed.

*Aspect.*—Smooth.

*Plant*

Form: Bush.

Growth: Medium, upright.

Foliage: 5 to 7 leaflets.

*Size.*—Medium.

*Quantity.*—Abundant.

*Color.*—New foliage: upper side—Calla Green, Plate 5, center—Mineral Red edges, Plate 27; under side—Bice Green, Plate 17. Old foliage: upper side—Dark Cress Green, Plate 31; under side—Light Cress Green, Plate 31.

*Shape.*—Oval.

*Texture.*—Upper side—leathery. Under side—smooth. Ribs and veins—ordinary.
*Edge.*—Serrated (saw toothed).
*Serration.*—Single, small.
*Rachis.*—Color—Cress Green, Plate 31. Under side—smooth.
*Stipules.*—Long, bearded.
*Disease resistance.*—Resistant.

Wood:

*New wood.*—Bice Green, Plate 17. Bark—smooth.
*Old wood.*—Cress Green, Plate 31. Bark—smooth.

Thorns (thorns are divided into thorns, prickles, and short needles):

*Thorns.*—Quantity:—On main stalks from base—ordinary; on laterals from stalk—ordinary. Form—narrow base, medium length (hooked downward). Color when young—Mikado Brown, Plate 29. Position—irregular.
*Prickles.*—Quantity:—On many stalks—few; on laterals—few. Color—Mikado Brown, Plate 29.
*Short needles.*—Quantity:—on main stalks—few; on laterals—few.

Asexual reproduction shows that the distinguishing characteristics of this new rose as herein given come true to form in succeeding propagations.

I claim:

A new and distinct variety of Hybrid Tea Rose plant characterized by the deep rich red color of its flower changing to deep Carmine, the symmetrical form of bud and half open flower for a rose of this coloring, the notched form of the petals, the habit of growth and coloring of the wood, foliage and thorns, substantially as shown and described.

L. PAHISSA.